United States Patent [19]
Patel et al.

[11] Patent Number: 6,051,242
[45] Date of Patent: *Apr. 18, 2000

[54] QUICK-DRYING COATING COMPOSITIONS

[75] Inventors: Mukesh Patel, Voorhees; Larry W. Steffier, Cherry Hill, both of N.J.

[73] Assignee: Mycone Dental Corporation, Cherry Hill, N.J.

[*] Notice: This patent is subject to a terminal disclaimer.

[21] Appl. No.: 08/876,347

[22] Filed: Jun. 16, 1997

Related U.S. Application Data

[63] Continuation-in-part of application No. 08/434,146, May 2, 1995, Pat. No. 5,639,447.

[51] Int. Cl.$^7$ .............................. A61K 6/00; A61K 7/00; A61K 7/04
[52] U.S. Cl. .............................. 424/401; 424/61
[58] Field of Search ........................ 424/401, 61

[56] References Cited

U.S. PATENT DOCUMENTS

| | | |
|---|---|---|
| 2,173,755 | 9/1939 | Fuller . |
| 3,483,289 | 12/1969 | Michaelson et al. . |
| 3,574,822 | 4/1971 | Shepherd et al. . |
| 3,749,769 | 7/1973 | Sugiyama et al. . |
| 3,773,710 | 11/1973 | Victorius . |
| 3,780,003 | 12/1973 | Seymour et al. . |
| 3,846,368 | 11/1974 | Pettit, Jr. . |
| 3,926,892 | 12/1975 | Holcombe, Jr. . |
| 3,928,113 | 12/1975 | Rosenberg . |
| 3,967,045 | 6/1976 | Kurobe et al. . |
| 4,058,442 | 11/1977 | Lee, Jr. et al. . |
| 4,097,589 | 6/1978 | Shansky . |
| 4,126,675 | 11/1978 | Boulogne et al. . |
| 4,179,304 | 12/1979 | Rossomondo . |
| 4,229,227 | 10/1980 | Ikeda et al. . |
| 4,229,431 | 10/1980 | Lee, Jr. et al. . |
| 4,260,701 | 4/1981 | Lee, Jr. . |
| 4,301,046 | 11/1981 | Schlossman . |
| 4,396,476 | 8/1983 | Roemer et al. . |
| 4,421,881 | 12/1983 | Benkendorf et al. . |
| 4,596,260 | 6/1986 | Giuliano . |
| 4,626,428 | 12/1986 | Weisberg et al. . |
| 4,649,045 | 3/1987 | Gaske et al. . |
| 4,669,491 | 6/1987 | Weisberg et al. . |
| 4,683,007 | 7/1987 | Horowitz et al. . |
| 4,712,571 | 12/1987 | Remz et al. . |
| 4,740,370 | 4/1988 | Faryniarz et al. . |
| 4,747,419 | 5/1988 | Flynn et al. . |
| 4,749,564 | 6/1988 | Faryniarz et al. . |
| 4,766,005 | 8/1988 | Montgomery et al. . |
| 4,798,720 | 1/1989 | Holder . |
| 4,820,509 | 4/1989 | Yamazaki et al. . |
| 4,863,993 | 9/1989 | Montgomery . |
| 4,871,534 | 10/1989 | Montgomery . |
| 4,897,261 | 1/1990 | Yamazaki et al. . |
| 5,045,309 | 9/1991 | Dell'Aquila . |
| 5,093,108 | 3/1992 | Pappas et al. . |
| 5,098,696 | 3/1992 | Montgomery . |
| 5,098,952 | 3/1992 | Blasko et al. . |
| 5,118,495 | 6/1992 | Nafziger et al. . |
| 5,130,125 | 7/1992 | Martin et al. . |
| 5,174,996 | 12/1992 | Weber et al. . |
| 5,206,011 | 4/1993 | Pappas et al. . |
| 5,275,807 | 1/1994 | Pappas et al. . |
| 5,456,905 | 10/1995 | Valenty . |
| 5,523,076 | 6/1996 | Schoon . |
| 5,639,447 | 6/1997 | Patel .......................... 424/61 |
| B1 4,596,260 | 7/1988 | Giuliano . |

FOREIGN PATENT DOCUMENTS 1 952 721  10/1969  Germany .

*Primary Examiner*—Thurman K. Page
*Assistant Examiner*—Sharon Howard
*Attorney, Agent, or Firm*—Atkin, Gump, Strauss, Hauer & Feld, L.L.P.

[57] ABSTRACT

Quick drying coating compositions, preferably but not exclusively for application to natural or artificial nails are provided. The quick-drying coating composition comprises a base or lacquer component and an optional pigment component. The base component can dry in less than about 70 seconds under ambient conditions, yet is free of undesirable solvents and components such as acetone, toluene, chlorinated hydrocarbons, and formaldehyde-containing resins. The base component includes film-forming polymers, a monomer component compatible with the polymers, and a free radical source.

27 Claims, No Drawings

QUICK-DRYING COATING COMPOSITIONS

CROSS REFERENCE TO RELATED APPLICATION

This patent application is a continuation-in-part of application Ser. No. 08/434,146 filed May 2, 1995, now U.S. Pat. No. 5,639,447.

BACKGROUND OF THE INVENTION

The present invention relates to quick-drying coating compositions, and preferably to coating compositions for application to natural or artificial fingernails or toenails under ambient conditions.

Numerous types of coating compositions, and particularly liquid nail coating formulations, are sold commercially. Liquid nail coating formulations typically contain a primary film former such as nitrocellulose, a secondary film former such as toluene-sulfonamide-formaldehyde resin, a plasticizer such as camphor or dibutyl phthalate, and one or more solvents such as toluene (toluol), lower aliphatic alcohols, and acetates. In addition, these formulations usually contain coloring agents and fragrances.

There are a number of desirable properties which nail coating compositions such as nail polish should possess. In particular, a nail polish should dry and harden quickly, apply easily, be adherent, glossy, waterproof and suitably colored, wear well, be elastic, resist chipping, peeling and abrasion for a reasonable period of time, and be dermatologically innocuous. In addition, nail polish formulations should exhibit good shelf stability and resist separation or settling out of their components, e.g., pigment components.

An important property of a nail coating such as a nail polish is its ability to dry rapidly when applied to a natural human, or even in some instances, natural animal (such as dogs) or artificial fingernail or toe nail. In practice, this rapid-drying property is difficult to achieve while retaining the other desirable characteristics such as gloss, wear resistance, etc. The coating process, however, can be time consuming since a coating of polish must dry before a subsequent coating can be applied to the first coating. Since the average drying time for a coating of conventional nail polish is about five minutes, the total time for completing the nail polishing process using conventional coating compositions can be 15 minutes or more.

The time consuming aspects of applying nail polish is of particular concern to women who work outside the home. These women need to have a product which can be easily applied and which dries in the shortest amount of time. Also, in the manicure and pedicure industries such as nail care and beauty salons, a nail polish which can dry in a period less than about one minute would provide a significant advantage over the prior art compositions.

The art has attempted to reduce the time required for drying of nail polishes. Such prior art nail coating compositions generally use solvent systems that are relatively volatile under ambient conditions. The term "under ambient conditions" as used herein refers to ambient temperature and humidity conditions typical of indoor environments, i.e., about 15° C. to 25° C. (about 59° F. to about 77° F.) and about 20% to 70% relative humidity.

A preferred volatile solvent in prior art nail coating composition is acetone, but acetone has several drawbacks when used in nail coating formulations. Besides being highly flammable, acetone in nail coating formulations causes bottleneck fouling in nail polish bottles with repeated use and causes difficulty in coating leveling when applied with a nail polish brush. Acetone is a hygroscopic solvent, so water contamination from atmospheric moisture often renders the polish unusable after the nail polish bottle has been opened for use several times. An additional drawback is that severe pigment discoloration is observed with acetone-containing nail polish formulations that are exposed to elevated temperature above ambient conditions.

Other components present in prior art nail coating compositions are known environmental or health hazards, being chemicals that are detrimental to air quality or are suspected human carcinogens or are toxic to humans. For example, prior art nail coating compositions that rely on volatile solvents such as acetone to obtain rapid drying once the composition is applied to nails result in undesirable volatile organic carbon (VOC) emissions that contribute to air pollution.

Toluene, a component that allows nail coating lacquers to dry to high gloss films with good fingernail-adhesion properties, is moderately toxic through skin absorption or inhalation and is an embryofetatoxin. Chlorinated hydrocarbon solvents, such as methylene chloride, trichlorethane, methyl chloroform and the like, often used in nail coating formulations to reduce drying time and increase compatibility of other components in the formulation, are cancer suspect agents and are known to be detrimental to the environment, particularly to the ozone layer. Formaldehyde-containing resins are used in some prior art nail polish formulations to impart flexibility and good fingernail-adhesion properties but are undesirable due to the presence of formaldehyde, a suspected human carcinogen. Other known solvent systems contain acetone, which is added to standard nail polish formulations to substantially hasten drying of a nail enamel composition to a durable, hard finish, but acetone is a highly volatile and noxious solvent.

A need therefore continues for coating formulations, especially nail coating formulations, which can dry rapidly and which overcome the disadvantages of the art, by omitting detrimental or undesirable components such as those described above.

SUMMARY OF THE INVENTION

One aspect of the present invention relates to a coating composition which, when applied as a coating to a substrate, dries in time periods of less than about 70 seconds under ambient conditions. The quick-drying coating compositions of the invention comprise a base or lacquer component having about 5% to about 40% by weight primary film-forming polymer; about 1% to about 30% by weight secondary film-forming polymer; about 0.1% to about 20% by weight reactive species that is compatible with the film-forming polymers; about 0.1% to about 6.0% by weight of at least one plasticizer; about 8% to about 80% solvent system, and a catalytically effective amount up to about 2% by weight free radical source, wherein the amounts are based on the total weight of the base composition.

In another aspect, the coating compositions may include a pigment component. The pigment component can comprise a pigment, a brightening agent, a primary film former, solvent, thixotropic agent, plasticizer and an aromatic ketone selected from the group consisting of 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl.

The coating compositions of the invention are preferably nail coatings and provide substantial advantages over the art.

For example, the compositions of the invention dry in less than about 70 seconds without streaking or smudging. Other advantages will become apparent from the detailed description.

DETAILED DESCRIPTION OF THE INVENTION

The coating compositions of this invention are preferably nail treatment compositions, but the invention also includes within its scope coating compositions intended for application to other substrates, e.g., metal surfaces that are bare metal or that contain base coats, such as automotive coatings, coatings for appliances or any other industrial, commercial or consumer product. This detailed description of the invention relates to the preferred embodiments as nail treatment compositions; but one skilled in the art will be able to adapt or apply the coatings of the invention to other purposes in view of the present disclosure.

The coating compositions of the invention can be formulated as a clear, colorless base or lacquer component, optionally mixed with a pigment component when a colored coating is desired. The base or lacquer component comprises a low boiling point solvent system, primary and secondary film formers, a reactive species component, such as a monomer, oligomer or polymer, that is compatible with the primary and secondary film formers, a free radical source, at least one plasticizer and an optional thixotropic agent. The pigment component comprises pigments, a primary film former, a brightening agent, an optional thixotropic agent, plasticizer, aromatic ketones, and solvents.

The base, or lacquer, component can include about 5% to about 40%, preferably about 12% to about 19%, more preferably about 7% to about 11% by weight, and most preferably about 5% of a primary film-forming polymer; about 1% to about 30%, preferably about 7% to about 18%, and most preferably about 12% by weight of a secondary film-forming polymer; about 0.1% to about 20%, more preferably about 2% to about 10%, and most preferably about 3 to about 8% by weight monomer or other reactive species that is compatible with the film-forming polymers; about 0.1% to about 6%, preferably about 0.1% to about 0.9%, and most preferably about 0.3% by weight of at least one plasticizer; about 8% to about 80% of a solvent system, preferably about 45% to about 55% solvent system; and a catalytically-effective amount up to about 2%, preferably about 0.1% to about 1%, most preferably about 0.1% to about 0.4% by weight free radical source, wherein the above percentages are based on the total weight of the base component. The amount of secondary film-forming polymer in the base component is effective to strengthen the primary film-forming polymer and to provide a film having an effective gloss and adhesion.

The amounts of primary film former and secondary film former are chosen to produce a hardened coating thickness of about 0.0001 inch to about 0.005 inch, preferably about 0.001 inch to about 0.003 inch.

Primary film-forming polymers useful in the base, or lacquer, component include any of nitrocellulose, cellulose acetate butyrate, cellulose acetate propionate, cellulose acetate, ethyl cellulose, acrylic polymer or vinyl polymer, including modifications and derivatives of these film-forming polymers that have polymerizable moieties, capable of reacting with the reactive monomer, oligomer or polymer component. The primary film-forming polymers provide body and viscosity functionality in the base composition. Primary film-formers useful in the base component are selected for their hardness, toughness, resistance to abrasion and ability to release solvent rapidly.

Nitrocellulose is especially preferred as a primary film-forming polymer. Other preferred primary film-forming polymers include cellulose acetate butyrate, cellulose acetate propionate, cellulose acetate and ethyl cellulose. Useful primary film formers include nitrocellulose, particularly lower molecular weight resins such as RS nitrocellulose. Nitrocellulose may be employed in a concentration of about 70% based on the weight of the base component, wet with about 30% ethanol or isopropanol.

Nitrocelluloses useful in the base component are readily available commercially and have viscosity grades SS/2 or RS ¼ sec. The RS ¼ sec. grade has a high solids content. Other useful viscosity grades include RS ½ sec. which has a high non-volatile content, as well as the RS 5 sec., RS 6 sec., RS 60 sec., and the RS 80 sec. grades. RS nitrocellulose is presently preferred.

The term RS refers to the RS nitrocellulose that has a nitrogen content of about 11.2% to about 12.8% and is soluble in esters, ketones and glycol ethers. RS nitrocellulose is available from Hercules, Inc., Wilmington, Del., U.S.A., among other suppliers. The terms ¼ sec., ½ sec., 5 sec., etc. represent measurements of viscosity and refer to the time (in seconds) it takes for a ball to fall to a given depth in the material.

Secondary film formers useful in the base component are chosen on the basis of their ability to build film and to enhance the depth, gloss and adhesion of the applied coating. Useful secondary film formers include but are not limited to celluloses such as ethyl cellulose, cellulose acetate, cellulose acetate butyrate and cellulose acetate propionate; vinyl polymers such as polyvinyl acetate and polyvinyl butyrate; polyether urethanes such as polyurethane resins; and polyester resins, particularly acrylic polymers such as methacrylate polymers, copolymers and terpolymers and acrylate polymers, copolymers and terpolymers, preferably formed from hydrophilic monomers, e.g., polyethyl acrylate, polyethyl methacrylate, polyhydroxyethyl methacrylate, polyglycidyl methacrylate, polymethacrylic anhydride, polyethoxylated dimethacrylates, polyethylene glycol acrylates and methacrylates, and terpolymers containing less than about 20% by weight of hydrophobic aliphatic or aromatic monomer constituents such as lauryl methacrylate, stearyl methacrylate or the like. Preferably, polyethyl acrylate and/or polyethyl methacrylate in an amount of about 7% to about 11% by weight of the base component can be employed as the secondary film-forming polymer. Other polyester resins which may be employed can be obtained from mixtures of 2,2,4-trimethyl-1,3-pentanediol, isophthalic acid-85, and trimellitic anhydride. The polyester resins can be formed by combining these constituents in the presence of a catalyst such as a dibutyl tin oxide by methods known in the art.

The reactive species component is preferably a monomer component but may also be an oligomeric component or a reactive polymeric component, or a combination of these. The reactive species should be compatible with the primary and secondary film formers in the formulation and should be reactive with at least one of the film-formers once the formulation is applied as a thin-film coating to a substrate under normal conditions of use.

The monomer component that is a reactive species is a monomer that is compatible with the (primary and/or secondary) film-forming polymers; preferred monomers are aliphatic and aromatic monomers. The monomer is preferably an "ethylenic" monoethylenically or polyethylenically unsaturated monomer, particularly an acrylate, methacrylate, acrylic acid, methacrylic acid, or a substituted derivative thereof. Other such "ethylenic" monomers include acrylamides, methacrylamides, acrylonitriles, vinyl halides and acetates, and mixtures of any of them. The monomer may also be a "styrenic" monoethylenically unsaturated monomer, such as styrene and aliphatic- and halogen-substituted styrene. In conjunction with these ethylenic and styrenic monomers, other monoethylenically unsaturated comonomers may also be used such as dialkyl maleate, dialkyl fumarate, dialkyl crotonate, dialkyl itaconate, dialkyl glutaconate, and the like.

Monomers that include monofunctional acrylate and methacrylate monomers are preferred, e.g., alkyl acrylates and methacrylates, cycloaLkyl, aralkyl and aryl acrylates and methacrylates. Such acrylate and methacrylate monomers can include allyl methacrylate, benzyl acrylate, caprolactone acrylate, cyclohexyl acrylate, cyclohexyl methacrylate, 2-ethoxyethyl acrylate, 2-ethoxyethyl methacrylate, 2(2-ethoxyethoxy) ethylacrylate, glycidyl methacrylate, hexyl acrylate, n-hexyl methacrylate, cyclohexyl methacrylate, isobornyl acrylate, isobornyl methacrylate, isodecyl acrylate, isodecyl methacrylate, isooctyl acrylate, lauryl acrylate, lauryl methacrylate, 2-methoxyethyl acrylate, octyl acrylate, 2-phenoxyethyl acrylate, 2-phenoxyethyl methacrylate, stearyl acrylate, stearyl methacrylate, tetrahydrofurfuryl acrylate, tetrahydrofurfuryl methacrylate, tridecyl methacrylate, 2-ethyl hexyl methacrylate and 2-ethylhexyl acrylate.

Other suitable monomers include hydroxymethyl methacrylate, hydroxypropylmethacrylate, propylene glycol monoacrylate, propylene glycol monomethacrylate, glycerol methacrylate, sorbitol methacrylate, and the like.

Still other monomers include anhydrides like methacrylic anhydride, maleic anhydride, itaconic anhydride, and the like.

The monomer component may also include difunctional acrylates and methacrylates, examples of which are as follows: Acrylate terminated monomers with average chain length of $C_{14}-C_{15}$, bisphenol A dimethacrylate, 1,4 butanediol diacrylate, 1,4 butanediol dimethacrylate, 1,3 butylene glycol diacrylate, 1,3 butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6 hexanediol diacrylate, 1,6 hexanediol dimethacrylate, methacrylate terminated monomer with average chain length of $C_{14}-C_{15}$, neopentyl glycol diacrylate, neopentyl glycol dimethacrylate, polyethylene glycol (200) diacrylate, polyethylene glycol dimethacrylate, tetraethylene glycol diacrylate, tetraethylene glycol dimethacrylate, triethylene glycol diacrylate, triethylene glycol dimethacrylate and tripropylene glycol diacrylate.

The monomer component may also include multifunctional, i.e., polyfunctional, acrylates and methacrylates, and these are preferred monomeric components. Examples are as follows: dipentaerythritol pentaacrylate, ethoxylated pentaerythritol triacrylate, pentaerythritol tetraacrylate, pentaerythritol triacrylate, trimethylolpropane triacrylate, trimethylolpropane trimethacrylate, tris (2-hydroxy ethyl) isocyanurate triacrylate and tris(2-hydroxy ethyl) isocyanurate trimethacrylate.

Suitable oligomeric and polymeric reactive species that may be used in lieu of or in combination with the reactive monomer component include aliphatic and aromatic urethane diacrylates, silcone acrylates, epoxy acrylates, polyester acrylates and the like.

The monomer component or other reactive species in the coating compositions of this invention provides several unexpected benefits to the formulations, not present in prior art coating formulations, e.g., prior art nail coatings. The monomer or other reactive species component provides solvent functionality to the composition, increasing the compatibility of the components present in the composition. However, when the coating composition is applied as a thin film coating to a substrate such as nails or the like, the monomer component provides different functionality by becoming reacted with the polymer film-forming components and thus becomes an integral element of the dry coating that results. The volatile solvents conventionally used in prior art coating formulations, on the other hand, are released as VOC into the atmosphere upon drying of the applied coating, an environmentally undesirable result.

The monomer or other reactive species used in Applicants' invention provides solvent functionality so that the concentration of conventional solvents in the formulation may be reduced. In addition, the presence of the monomer or other reactive species component eliminates the need for conventional but undesirable solvents, such as acetone, toluene, chlorinated hydrocarbons and formaldehyde-containing resins, since the monomer component not only provides solvating and compatibilizing functionality, but also contributes to film forming and nail-adhesion functionality in the resultant nail coating.

The coating compositions of this invention, particularly the nail treatment compositions, exhibit unexpectedly long shelf stability, as compared with conventional coating formulations. When subjected to accelerated shelf life testing at a temperature of 130° F. (54° C.), conventional nail coating formulations typically exhibit separation of ingredients after about 3–14 days. By contrast, coating compositions according to the present invention have been shown to be stable under similar test conditions for significantly longer periods, over 80 days, with ingredient separation only becoming very evident at 120 days.

The excellent shelf stability of the coating compositions of this invention is especially remarkable since the compositions contain a monomer component, or other reactive species, and free radical source yet do not require the post addition of a polymerization inhibitor. The above-mentioned long-term shelf stabilities are obtained without the presence of polymerization inhibitors, to retard polymerization of the monomer component while the composition is in a container such as a nail polish bottle. Polymerization inhibitors are preferably absent or present only at very low concentrations in the coating compositions of this invention since inhibitor levels typically used in the prior art to prevent premature monomer polymerization would be detrimental to the reaction of the monomer with the film-forming polymers, once the coating composition of this invention is applied as a thin film coating to a substrate such as a nail.

Free radical sources or other drying accelerators for use in the base component are effective to cause the base composition to dry in an ambient atmosphere in less than about 70 seconds. Free radical sources may be any monomer-soluble or oil-soluble catalyst, peroxide catalysts being preferable, e.g., alkanoyl, aroyl, alkaroyl, and aralkanoyl diperoxides and monohydroperoxides, dialkyl peroxides, methyl ethyl ketone peroxides, peroxyesters, percarbonates, peroxydicarbonates, peroxyketals and the like. Benzoyl peroxide is a preferred peroxide free radical source. Other free radical sources such as azo compounds may also be used as the catalyst. Other free radical sources known to those skilled in the polymer art may likewise be used.

The free radical source or drying accelerator may be used in amounts of from a trace amount that is catalytically effective (i.e., about 1 ppm or more based on the monomer weight) up to about 2%, preferably about 0.1% to about 1%, most preferably about 0.1% to about 0.4% by weight, based on the weight of the base component. The free radical source facilitates reaction of the monomer component (or reactive oligomer or polymer) with the film-forming polymers in the base component, once the composition is applied as a thin film coating to a substrate such as a nail. A "catalytically effective" amount is an amount of free radical source sufficient to effect reaction of the monomer such that the applied composition has the property of drying in less than about 70 seconds.

The free radical source may be added to the base composition as a separate component or may be added in combination with one or more of the other components, e.g., in combination with a film-forming polymer.

The base composition may also contain UV absorbers such as benzophenone, which serve as anti-yellowing agents.

Solvent systems suitable for use in the base component typically include ethyl acetate with at least one of isobutyl acetate and butyl acetate. High-boiling point solvents such as xylene and heptane may be added to the solvent system, but care must be taken to limit the use of such solvents to low levels to avoid increasing the drying time above acceptable limits. An acceptable drying time for the base component is less than about 70 seconds.

Other useful solvent systems for use in the base component include mixtures of lower alkyl acetates, lower alkyl alcohols, and lower alkyl ketones; the term "lower alkyl" refers to $C_1$–$C_4$ alkyls. Preferably, the solvent system includes about 5% to about 50%, preferably about 20% to about 45% ethyl acetate; about 3% to about 50%, preferably about 15% to about 35% isobutyl acetate or butyl acetate; up to about 20%, preferably about 0.2% to about 11% isopropanol or ethanol; and about 0.5% to about 30%, preferably about 10% to about 20% methylethyl ketone, based on the weight of the solvent system.

The solvent system employed in this invention preferably does not contain undesirable or detrimental solvents such as acetone, toluene, chlorinated hydrocarbons such as methylene chloride, trichlorethane or methyl chloroform, or formaldehyde-containing resins.

Plasticizers employed in the base component are chosen to impart flexibility to the hardened coating, particularly, nail treatment coatings. The choice of plasticizer may vary as a function of the color, odor, effect on viscosity of the enamel, effect on the drying rate, the amount needed to meet flexibility requirements, the volatility of the plasticizer, as well as compatibility with the other components of the compositions.

Plasticizers which may be used in the base component include, without limitation, dibutyl phthalate, butyl phthalate, butyl glycolate, triphenyl phosphate, tricresyl phosphate, diamylphthalate, dibutyl phthalate, diethyl phthalate, dibutoxy ethyl phthalate, dioctyl phthalate, castor oil, benzyl benzoate, tributyl phosphate, butyl acetyl ricinoleate, butyl stearate, triethyl citrate, dibutyl tartrate and diamyl phthalate. Preferably, dibutyl phthalate is the plasticizer. The plasticizer, e.g., dibutyl phthalate, is preferably employed in the base component in an amount of about 0.1% to about 0.9%, preferably about 0.2% to about 0.5%, most preferably about 0.3% by weight of the base component.

The base, or lacquer, component employed in the invention may also include an optional thixotropic agent in an amount effective to gel the composition. The thixotropic agent may comprise one or more thixotropic agents, and, if a pigment composition is used with the base composition, the thixotropic agent hay also provide such functionality for the pigment composition as well. Useful thixotropic agents, which may also be called thickeners, include stearalkonium hectorites such as Bentone™ 27, Bentone™ 28, especially Bentone™ 27. Typically, the optional thixotropic agent is present in an amount of about 0.1% to about 5%, preferably about 0.2% to about 0.4% by weight, based on the total weight of the base component. Preferably, the lacquer component includes about 0.2% to about 0.3% by weight Bentone™ 27 based on the weight of the base component. Bentone™ thickeners are available from Rheox, Inc., Hightstown, N.J. 08520, U.S.A.

In another aspect of the invention, a pigment component can be mixed with the base, or lacquer, component to provide colored, rapid drying coating compositions, such as a nail polish. The amount of pigment component may be about 0.5% to about 50%, typically about 0.5% to about 35% by weight, based on the combined weight of the base or lacquer component and the pigment component.

The pigment component comprises pigment, brightening agent, plasticizer, primary film former, optional secondary film former, thixotropic agent, solvent and aromatic ketone. Choice of pigment is based on the desired color of the polish. Useful pigments include but are not limited to D & C Red #6, #7, #9, #10, #30, #33 and #34 Lakes, D & C Yellow #5 Lakes, titanium dioxide, mica, iron oxides, iron black aluminum silicate and iron blue aluminum silicate. In addition to the above-named pigments, iridescent additives such as "pearl essence" which is a suspension of crystalline guanine in nitrocellulose and solvents may be employed. Especially useful pigments include D & C pigments, titanium dioxide, and mica. The amount of pigment in the pigment component may be about 1% to about 85%, preferably about 30% to about 45% by weight, based on the total weight of the pigment component.

Useful brightening agents include bismuth oxychloride, hydrated alumina and preferably bismuth oxychloride, and such brightening agents may be used in an amount of about 1% to about 18%, preferably about 2% to about 8%, most preferably about 4% to about 5% by weight, based on the total weight of the pigment component.

Plasticizers which may be used in the pigment component include camphor, dibutyl phthalate and preferably camphor, and such plasticizers may be used in an amount of about 0.1% to about 6%, preferably about 0.8% to about 1% by weight, based on the total weight of the pigment component.

The thixotropic agent included in the pigment component enhances suspension of pigment and the other components of the pigment component composition. Although a number of thixotropic agents may be employed in the pigment component, preferred thixotropic agents include thixotropic clays, preferably stearalkonium hectorites such as Bentone™ thickeners, more preferably Bentone™ 27. The amount of thixotropic agent in the pigment component may be about 0.1% to about 5%, preferably about 0.2% to about 2%, and more preferably about 0.3% to about 0.9% by weight, based on the total weight pigment component, depending on the nature and type of pigment and other ingredients forming the pigment component. When the coating composition of this invention comprises a base component and pigment component, the thixotropic agent employed in the pigment component may also serve as the optional thixotropic agent or thickener for the base, or lacquer, component as well.

The primary film former employed in the pigment component is believed to function as a binder for the pigment employed in the pigment component. Useful primary film formers include nitrocelluloses such as those mentioned above for use as the primary film-forming polymer in the base component. The primary film former can optionally be combined with secondary film formers such as those employed in the base component. Nitrocellulose, however, is preferably employed alone. The amount of nitrocellulose employed in the pigment component may be about 5% to about 40%, preferably about 2% to about 18%, most preferably about 16% by weight, based on the total weight of the pigment component.

Solvents useful in the pigment component include lower alkyl acetates, preferably isobutyl acetate and ethyl acetate, in amounts of about 1% to about 50%, preferably about 30% to about 45% by weight, based on the total weight of the pigment component. Other useful solvents include butyl acetate and equivalent solvents well known to those skilled in the coating art. Detrimental solvents as discussed above, such as acetone, toluene, chlorinated hydrocarbon solvents and the like, are preferably absent from the solvent system used for the pigment component.

Exemplary aromatic ketones useful in the pigment component include 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl. The aromatic ketones may comprise about 0.01% to about 1% by weight, based on the total weight of pigment component. Preferably, the aromatic ketone is 2-hydroxy-2-methyl-1-phenyl-propane-1-one in an amount of about 0.2% to about 0.3% by weight of the pigment component.

In formulating the base, or lacquer, component, solvents are mixed to produce a low boiling point solvent system. The monomer component of the base component is then added to the solvent system. Thereafter, a primary film-forming polymer, a secondary film-forming polymer and at least one plasticizer are added stepwise in any order in conjunction with vigorous mixing until a viscous solution is produced. After the viscous solution is produced, an optional thixotropic agent may be added, if desired, to the solution in conjunction with vigorous stirring for a period sufficient to produce the base component.

In formulating the pigment component, a thixotropic agent is added to a solvent. Thereafter, the primary film former and the optional secondary film formers are added, followed by plasticizer. Pigments and aromatic ketones then are added.

In formulating pigmented coating compositions such as nail polishes, the pigment component is added to the base component. The pigment component is added to the base component to constitute about 0.5% to about 50%, preferably about 0.5% to about 35% by weight, based on the total weight of the pigmented composition. The rate of addition of the pigment component to the base component may vary over wide limits. Preferably the pigment component is added batch-wise to the base component to provide a mixture. The mixture then is subjected to mixing at about 180 rpm to about 250 rpm for about 20 to about 30 minutes in a Cowles mixer. The resulting average particle size of the pigment component typically is about 1 to about 8 microns. Preferably, the average particle size is the finest grind, as measured with a Gardner Grind Gauge (Hegman Gauge).

The coating compositions of the present invention, with or without the pigment component, have characteristics of quick-drying, flexibility, durability, adequate viscosity and high gloss. The coating compositions of the invention "dry" in a period of less than about 60 to about 80 seconds, preferably less than about 70 seconds. As used herein, "dry" is understood to mean that the compositions, when applied to a substrate such as a human or artificial nail, do not evidence tack (absence of smudging) after about 60 to about 80 seconds at room temperature (about 15–25° C. or 59–77° F.) and at a relative humidity of about 20% to about 60%.

The compositions of the invention are durable. Nail coating compositions of this invention typically do not chip or crack for a period of at least about three days of wearing on a human or synthetic nail. Coatings formed of the base component per se, as well as the coatings formed from compositions which include both the base and pigment components, exhibit an acceptable gloss.

The viscosities of the coating compositions of the invention, with or without the pigment component, are commercially acceptable. The static viscosities of the coating compositions of the invention are about 180 centipoise to about 480 centipoise, preferably about 250 centipoise. Static viscosities may be determined by Brookfield viscometer in a conventional manner. In addition to static viscosities, the shaken viscosities of the compositions of the invention are also commercially acceptable.

Each of the base and pigment components, as well as mixtures of the base and pigment components, are storage stable and may be satisfactorily applied to a substrate such as a human or artificial nail even after extended storage. There is no need to include, for example, a steel ball to enable a vigorous shaking of the composition before application as is required by many of the compositions of the prior art.

In order to evaluate the quick drying coating compositions prepared according to the invention, a series of nail polishes are prepared as described above and tested for drying times in Examples 1–4 below. Generally, in Examples 1–4, the base, or lacquer, component is produced by adding nitrocellulose, commercial grade polyethyl methacrylate, cyclohexyl methacrylate and dibutyl phthalate stepwise to a solvent system formed of ethyl acetate, isobutyl acetate, isopropyl alcohol, and methyl ethyl ketone by vigorous mixing until a viscous solution is produced. After the viscous solution is produced, Bentone™ 27 thixotropic agent is added to the solution in conjunction with vigorous stirring for a period sufficient to produce a gelled base component.

The pigment component employed in Examples 1–4 below is formulated by adding Bentone™ 27 to isobutyl acetate or ethyl acetate. Thereafter, nitrocellulose is added, followed by camphor. Pigments and aromatic ketones then are added.

The present invention will now be described in more detail with reference to the following specific, non-limiting examples.

EXAMPLES 1–4

In Examples 1–4, the coating compositions are prepared from various base or lacquer components and pigment components as described above. The base or lacquer component employed has one of the following exemplary compositions A-1, A-2 or A-3:

| LACQUER COMPONENT COMPOSITION | A-1 | A-2 | A-3 |
|---|---|---|---|
| Ethyl Acetate | 39.0% | 33.4% | 32.0% |
| Isobutyl Acetate | 21.3 | 24.1 | 22.8 |
| Isopropyl Alcohol | 6.0 | 6.5 | 6.0 |
| Methyl Ethyl Ketone | 11.5 | 13.5 | 16.1 |
| Nitrocellulose | 15.0 | 14.7 | 14.6 |
| Commercial Grade Polyethyl Methacrylate | 5.0 | 5.2 | 5.2 |
| Cyclohexyl Methacrylate | 1.3 | 1.6 | 2.2 |
| Dibutyl Phthalate | 0.3 | 0.4 | 0.5 |
| Benzoyl peroxide (approximate amount)* | 0.35 | 0.35 | 0.35 |
| Benzophenone | 0.4 | 0.3 | 0.4 |
| Bentone ™ 27 | 0.2 | 0.3 | 0.2 |
| Fragrance | (trace) | (trace) | (trace) |

*Free radical source was incorporated in polyethyl methacrylate polymer

The pigment component employed in the examples below has one of the following exemplary compositions B-1 or B-2:

| PIGMENT COMPONENT COMPOSITION | B-1 | PIGMENT COMPONENT COMPOSITION | B-2 |
|---|---|---|---|
| Bismuth Oxychloride | 4.5% | Bismuth Oxychloride | 4.0% |
| D & C #7 Pigment | 28.0 | D & C #6 Pigment | 15.0 |
| Blue D & C Iron Oxide | 0.7 | D & C #7 Pigment | 10.0 |
| Titanium Dioxide | 5.6 | Titanium Dioxide | 1.5 |
| 2-hydroxy-2-methyl-1-phenyl-propane-1-one | 0.2 | Yellow #5 | 20.5 |
|  |  | 2-hydroxy-2-methyl-1-phenyl-propane-1-one | 0.3 |
| Camphor | 1.0 | Camphor | 1.0 |
| Nitrocellulose | 14.0 | Nitrocellulose | 14.5 |
| Bentone ™ 27 | 0.3 | Bentone ™ 27 | 0.9 |
| Isobutyl Acetate | 45.7 | Ethyl Acetate | 32.3 |

The nail coating treatments are applied to human finger nails as a thin film coating of about 0.0001 inch thick. The films of nail coating, i.e., polish, are determined to be dry when they no longer smudge upon touching. The amount of time required for each film to dry is recorded. The compositions of the base or lacquer and pigment components, as well as the drying times of nail polishes produced from these components, are given in Table I:

TABLE I

| Example No. | Lacquer Component Composition (%)[1] | Pigment Component Composition (%)[1] | Drying Time[2] (Seconds) |
|---|---|---|---|
| 1 | A1-93% | B1-7% | 69 |
| 2 | A1-90% | B2-10% | 62 |
| 3 | A2-95% | B1-5% | 68 |
| 4 | A3-88% | B2-12% | 61 |

[1]Based on combined weights of the lacquer and pigment components.
[2]Measured on 0.0001 inch film thickness at 77° F. (25° C.) and 25% R.H.

The present invention may be embodied in other specific forms without departing from the spirit or essential attributes thereof and, accordingly, reference should be made to the appended claims, rather than to the foregoing specification as indicating the scope of the invention.

What is claimed is:

1. A quick-drying coating composition having the property of drying in less than about 70 seconds under ambient conditions, said composition having a base component comprising
    about 5% to about 40% by weight primary film-forming polymer;
    about 1% to about 30% by weight secondary film-forming polymer;
    about 1% to about 20% by weight reactive species compatible with the film-forming polymers;
    about 0.1% to about 6% by weight of at least one plasticizer;
    about 8% to about 80% by weight solvent; and
    a catalytically-effective amount up to about 2% by weight free radical source,
    said amounts based on total weight of the base component.

2. The composition of claim 1 wherein said primary film-forming polymer is selected from the group consisting of nitrocellulose, cellulose acetate butyrate, cellulose acetate propionate, cellulose acetate, ethyl cellulose, an acrylic polymer and a vinyl polymer.

3. The composition of claim 2 wherein the primary film-forming polymer is RS nitrocellulose.

4. The composition of claim 1 wherein said primary film former is present in an amount of about 12% to about 19% by weight.

5. The composition of claim 1 wherein said secondary film-forming polymer is selected from the group consisting of ethyl cellulose, cellulose acetate, cellulose acetate butyrate, cellulose acetate propionate, a vinyl polymer, a polyether urethane, a polyester resin and an acrylic polymer.

6. The composition of claim 1 wherein said secondary film former is an acrylic polymer selected from the group consisting of an acrylate polymer, copolymer and terpolymer; and a methacrylate polymer, copolymer and terpolymer.

7. The composition of claim 1 wherein said secondary film former is present in an amount of about 7% to about 18% by weight.

8. The composition of claim 1 wherein said reactive species is selected from the group consisting of a monomer, an oligomer and a polymer.

9. The composition of claim 1 wherein said reactive species is a monomer selected from the group consisting of an acrylic monomer, an acrylate monomer, a methacrylic monomer, a methacrylate monomer, an acrylamide monomer, a methacrylamide monomer, an acrylonitrile monomer, a vinyl halide monomer, a vinyl acetate monomer, a styrene monomer, a substituted derivative thereof, and mixtures thereof.

10. The composition of claim 9 wherein said monomer is selected from the group consisting of a monofunctional acrylate monomer; a difunctional acrylate monomer; a monofunctional methacrylic monomer; and a difunctional methacrylate monomer.

11. The composition of claim 1 wherein said reactive species is present in an amount of about 2% to about 10% by weight.

12. The composition of claim 1 wherein said free radical source is a peroxide compound.

13. The composition of claim 12 wherein said peroxide compound is selected from the group consisting of an alkanoyl, aroyl, alkaoyl, and aralkanoyl diperoxide, an alkanoyl, aroyl, alkaoyl, and aralkanoyl monohydroperoxide, a dialkyl peroxide, a methyl ethyl ketone peroxide, a peroxyester, a percarbonate, a peroxydicarbonate, and a peroxyketal.

14. The composition of claim 1 wherein said free radical source is present in an amount of about 0.1% to about 1% by weight.

15. The composition of claim 1 wherein said plasticizer is selected from the group consisting of dibutyl phthalate, camphor and mixtures thereof.

16. The composition of claim 1 wherein said plasticizer is present in an amount of about 0.1% to about 0.9%.

17. The composition of claim 1 which further comprises at least one thixotropic agent present in an amount effective to gel the base composition.

18. The composition of claim 17 wherein said thixotropic agent is present in an amount of about 0.1% to about 5%.

19. The composition of claim 1 wherein said solvent is selected from the group consisting of a lower alkyl acetate, a lower alkyl alcohol and an lower alkyl ketone.

20. The composition of claim 1 wherein said composition is essentially free of acetone, toluene and chlorinated hydrocarbon solvents.

21. The composition of claim 1 wherein said composition is a nail treatment formulation.

22. The composition of claim 1 wherein
said primary film-forming polymer is nitrocellulose,
said secondary film forming polymer is selected from the group consisting of cellulose acetate, cellulose acetate butyrate, cellulose acetate propionate and acrylic polymer,
said reactive species is a monomer selected from the group consisting of an acrylic monomer, a multifunctional acrylic monomer, a methacrylic monomer, and a multifunctional methacrylic monomer,
said free radical source is a peroxide compound, and
said solvent comprises ethyl acetate, at least one of isobutyl acetate and butyl acetate, at least one of isopropanol and ethanol, and methylethyl ketone.

23. A quick-drying coating composition comprising a base component and a pigment component, said composition having ability to dry in a period of less than about 70 seconds under ambient conditions,
said base component comprising the composition of claim 1; and
said pigment component comprising pigment, brightening agent, primary film former, solvent, thixotropic agent, plasticizer and an aromatic ketone.

24. The composition of claim 23 wherein said pigment component is present in an amount of about 0.5% to about 50% by weight, based on combined weight of the base and pigment components.

25. The composition of claim 23 wherein said pigment component comprises, based on total weight of said pigment component,
about 30% to about 45% by weight pigment;
about 2% to about 8% brightener;
about 5% to about 40% by weight primary film former, said primary film former comprising nitrocellulose;
about 30% to about 45% by weight solvent;
about 0.1% to about 5% by weight thixotropic agent;
about 0.2% to about 6% by weight plasticizer; and
about 0.01% to about 1% by weight aromatic ketone.

26. The composition of claim 23 wherein said pigment component comprises, based on total weight of said pigment component,
bismuth oxychloride as the brightener,
a solvent comprising an acetate selected from the group consisting of isobutyl acetate and ethyl acetate,
about 0.2% to about 2% stearalkonium hectorite as the thixotropic agent, about 0.2% to about 1% camphor as the plasticizer, and 2-hydroxy-2-methyl-1-phenyl-propane-1-one as the aromatic ketone.

27. The composition of claim 23 wherein said composition is a nail polish formulation.

* * * * *